(12) United States Patent
Lee et al.

(10) Patent No.: US 10,631,940 B2
(45) Date of Patent: Apr. 28, 2020

(54) SURGICAL PATH SETTING DEVICE, SURGICAL ROBOT SYSTEM COMPRISING SAME AND SURGICAL PATH SETTING METHOD FOR SURGICAL ROBOT

(71) Applicant: CUREXO, INC., Seoul (KR)

(72) Inventors: Sanghun Lee, Seoul (KR); Jaegeun Han, Seoul (KR); Junwoo Park, Yongin-si (KR)

(73) Assignee: CUREXO, INC., Seoul (KR)

( * ) Notice: Subject to any disclaimer, the term of this patent is extended or adjusted under 35 U.S.C. 154(b) by 284 days.

(21) Appl. No.: 15/579,269

(22) PCT Filed: May 10, 2016

(86) PCT No.: PCT/KR2016/004899
§ 371 (c)(1),
(2) Date: Dec. 4, 2017

(87) PCT Pub. No.: WO2016/195265
PCT Pub. Date: Dec. 8, 2016

(65) Prior Publication Data
US 2018/0161113 A1    Jun. 14, 2018

(30) Foreign Application Priority Data

Jun. 4, 2015  (KR) .......................... 10-2015-0078990

(51) Int. Cl.
*A61B 34/30* (2016.01)
*A61B 34/10* (2016.01)
(Continued)

(52) U.S. Cl.
CPC .............. *A61B 34/30* (2016.02); *A61B 34/10* (2016.02); *A61B 34/20* (2016.02); *A61B 34/70* (2016.02);
(Continued)

(58) Field of Classification Search
CPC ......... A61B 34/30; A61B 34/10; A61B 34/20; A61B 2034/107; A61B 2034/2055;
(Continued)

(56) References Cited

U.S. PATENT DOCUMENTS 5,408,409 A * 4/1995 Glassman ............... A61B 34/20
600/407
6,728,599 B2 * 4/2004 Wang ..................... A61B 34/70
128/897
(Continued)

FOREIGN PATENT DOCUMENTS

EP          1452147 A1    1/2004
JP       2003-114706 A    4/2003
(Continued)

OTHER PUBLICATIONS

Mitsuishi, Medical Robot and Master Slave System for Minimally Invasive Surgery, 2007, IEEE, p. 8-13 (Year: 2007).*
(Continued)

*Primary Examiner* — McDieunel Marc
(74) *Attorney, Agent, or Firm* — Novick, Kim & Lee, PLLC; Jae Youn Kim (57) ABSTRACT

A surgical path setting method, for a surgical robot, comprises the steps of (a) the surgical robot's operating a first surgical path that has been preset with respect to a surgical site of a person to be operated on; (b) the surgical robot's confirming whether or not a surgical path reset command, transmitted from a surgical path setting device, has been received; (c) the surgical robot's stopping if the surgical path reset command has been received; (d) the surgical path setting device's receiving an input of surgical path form information; (e) the surgical path setting device's determining a second surgical path, which is a new surgical path, on the basis of the surgical path form information and then
(Continued)

transmitting same to the surgical robot; and (f) the surgical robot's operating along the second surgical path.

15 Claims, 5 Drawing Sheets

(51) Int. Cl.
*A61B 34/20* (2016.01)
*A61B 34/00* (2016.01)

(52) U.S. Cl.
CPC . *A61B 2034/107* (2016.02); *A61B 2034/2055* (2016.02)

(58) Field of Classification Search
CPC ....... A61B 34/70; A61B 90/25; A61B 5/4533; A61B 34/77
See application file for complete search history.

(56) References Cited

U.S. PATENT DOCUMENTS

| | | | | |
|---|---|---|---|---|
| 6,836,703 B2* | 12/2004 | Wang | ...................... | A61B 34/77 318/568.11 |
| 6,839,612 B2* | 1/2005 | Sanchez | ................. | A61B 34/30 318/568.11 |
| 6,871,117 B2* | 3/2005 | Wang | ...................... | A61B 34/77 370/314 |
| 7,239,940 B2* | 7/2007 | Wang | ...................... | A61B 34/70 318/568.11 |
| 8,005,571 B2* | 8/2011 | Sutherland | ............. | A61B 90/25 700/248 |
| 9,763,683 B2* | 9/2017 | Bonutti | ................ | A61B 5/4533 |
| 2013/0345718 A1 | 12/2013 | Crawford et al. | | |

FOREIGN PATENT DOCUMENTS

| | | |
|---|---|---|
| JP | 2003-256025 A | 9/2003 |
| JP | 2004-254899 A | 9/2004 |
| JP | 2012-61529 A | 3/2012 |
| KR | 10-2010-0098055 | 9/2010 |
| KR | 10-2012-0099423 | 9/2012 |
| KR | 10-1195994 | 10/2012 |
| KR | 10-1334007 | 11/2013 |
| KR | 10-2014-0112208 | 9/2014 |
| KR | 10-2015-0001756 | 1/2015 |
| WO | 2009/092164 A1 | 7/2009 |
| WO | 2013/192598 A1 | 12/2013 |
| WO | 2014/151550 A2 | 9/2014 |

OTHER PUBLICATIONS

Knappe et al. Position control of a surgical robot by a navigation system, 2003, IEEE, p. 3350-3354 (Year: 2003).*
Chung et al. Development of SPINEBOT for spine surgery, 2004, IEEE, p. 3942-3947 (Year: 2004).*
Taylor et al. Medical robotics in computer-integrated surgery, 2003, IEEE, p. 765-781 (Year: 2003).*
Ashami et al., Optimal planning for minimally invasive surgical robots, 2003, IEEE, p. 854-863 (Year: 2003).*
Gueziec et al., Anatomy-based registration of CT-scan and intraoperative X-ray images for guiding a surgical robot, 1998, IEEE, p. 715728 (Year: 1998).*
International Search Report for International Application No. PCT/KR2016/004899, dated Aug. 18, 2016.

* cited by examiner

SURGICAL PATH SETTING DEVICE, SURGICAL ROBOT SYSTEM COMPRISING SAME AND SURGICAL PATH SETTING METHOD FOR SURGICAL ROBOT

TECHNICAL FIELD

The present invention relates to surgical path setting device, surgical robot system comprising the same, and surgical path setting method for surgical robot. More specifically, the surgical robot system permits to reset the surgical path of the surgical robot required during the surgery and the surgical path setting method is the operation of the surgical robot system.

BACKGROUND ART

Generally, the surgical robot refers to a robot capable of performing a surgical operation to replace a doctor. Advantageously, the surgical robot would operate more accurately and precisely as compared with a human and enable remote operation.

The surgical robots are classified into bone surgery robot, laparoscopic surgery robot, and orthopedic surgical robot depending on usage. The bone surgery robot is used for surgery to cut or join bones. The bone surgery robot has a higher accuracy of operation compared to a person's own operation with little hand shake. Also, it prevents the excessive radiation exposure from X-ray device for monitoring the operation progress and the stamina reduction of the medical worker from long-time surgery, advantageously.

Korea Patent NO. 2014-0112208A1 discloses surgery robot and control method thereof.

The conventional surgery robot operates the surgery along the determined surgical path automatically but it doesn't handle the outbreak situation during the surgery, for example, such that surgical site isn't confirmed before the surgery and overlooked during the surgical planning and thus the surgical path should be renewed.

DETAILED DESCRIPTION OF THE INVENTION

Technical Problem

An object of the present invention is to solve aforementioned problems, and to provide surgical path setting device, surgical robot system comprising the same, and surgical path setting method for surgical robot that permits to reset the surgical path when that surgical site was overlooked during the surgical planning and found during the surgery or the surgery should be operated with monitoring the surgical site directly.

Technical Solution

In order to achieve the above object, a surgical robot system in accordance to one aspect of the present invention, comprises: a surgical robot operating along a predetermined surgical path with respect to a surgical site of a patient; a surgical path setting device transmitting the surgical path to the surgical robot and transmitting a surgical path reset command to the surgical robot, if new surgical path should be set, to make the surgical robot stop the operation temporarily; and a tracking device confirming the positions of the patient and the surgical robot before surgery and tracking the positions of the patient and the surgical robot during surgery.

In order to achieve the above object, a surgical path setting device in accordance to another aspect of the present invention, transmits to a surgical robot a predetermined surgical path with respect to a surgical site of a patient to command the operation of the surgical robot, receives the positions of the patient and the surgical robot from a tracking device to set a surgical path before surgery, and resets new surgical path based on the surgical path form information during surgery. Here, the surgical path form information is any one of straight line, curve, plane, and curved surface.

In order to achieve the above object, a surgical path setting method, for a surgical robot in accordance to another aspect of the present invention, comprises the steps of: (a) the surgical robot's operating along a first surgical path that has been transmitted from a surgical path setting device and preset with respect to a body part of a person to be operated on; (b) the surgical robot's confirming whether or not a surgical path reset command, transmitted from the surgical path setting device, has been received; (c) the surgical robot's stopping the operation if the surgical path reset command has been received; (d) the surgical path setting device's receiving an input of surgical path form information; (e) the surgical path setting device's determining a second surgical path, which is a new surgical path, on the basis of the surgical path form information and then transmitting same to the surgical robot; and (f) the surgical robot's operating along the second surgical path.

Herein, the step (e) comprises: (e1) the surgical path setting device's first confirming the kind of the surgical path form information; (e2) the surgical path setting device's second confirming the kind of the surgical path form information according to the result of the first confirming, and determining the form of a second surgical path according to the result of the second confirming; (e3) the surgical path setting device's confirming the location and the number of multiple surgical path reset positions; (e4) the surgical path setting device's determining the second surgical path including the plurality of the surgical path reset positions according to the determined form and the result of the confirming; and (e5) the surgical path setting device's transmitting the determined second surgical path to the surgical robot.

Also, the step (e1) can comprises: the surgical path setting device's determining one of straight line, curve, plane, and curved surface for surgical path form according to the result of the first confirming.

Also, the step (e2) can comprises:

the surgical path setting device's second confirming whether the surgical path form is a path designation or specific direction designation if the first confirmed surgical path form is straight line and determining the form of the second surgical path based on the result of the second confirming;

the surgical path setting device's second confirming whether the surgical path form is arc or free curve if the first confirmed surgical path form is curve, and determining the form of the second surgical path based on the result of the second confirming;

the surgical path setting device's second confirming whether the surgical path form is region designation or surface designation if the first confirmed surgical path form is plane, and determining the form of the second surgical path based on the result of the second confirming; or the surgical path setting device's second confirming whether the surgical path form is spherical surface or designated curved surface if the first confirmed surgical path form is curved surface, and determining the form of the second surgical path based on the result of the second confirming.

Advantageous Effects of the Invention

According to the present invention permitting to reset the surgical path during the surgery with the surgical robot, the possibility of the accident during the surgery is reduced and the accuracy of the surgery is enhanced.

MODE FOR EMBODIMENT OF THE INVENTION

Hereinafter, exemplary embodiments of the seating-type walk rehabilitation robot according to the present invention will be described in detail referring to the appended drawings. The present invention is not limited to the embodiments that will be described below and can be implemented in different ways. These embodiments are provided only to explain the present invention and to tell the scope of the invention to those of ordinary skill in the art.

Figure 1:
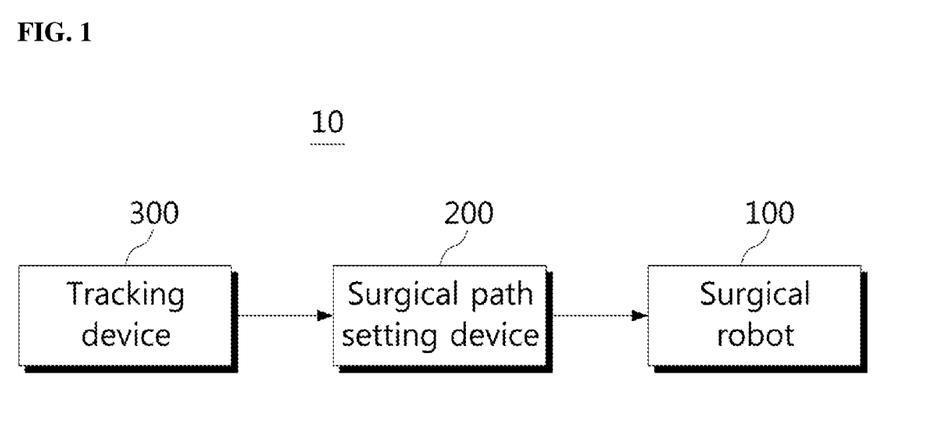
FIG. 1 is the control block diagram of the surgical robot system in accordance to the preferable embodiment of the present invention.
Figure 2:
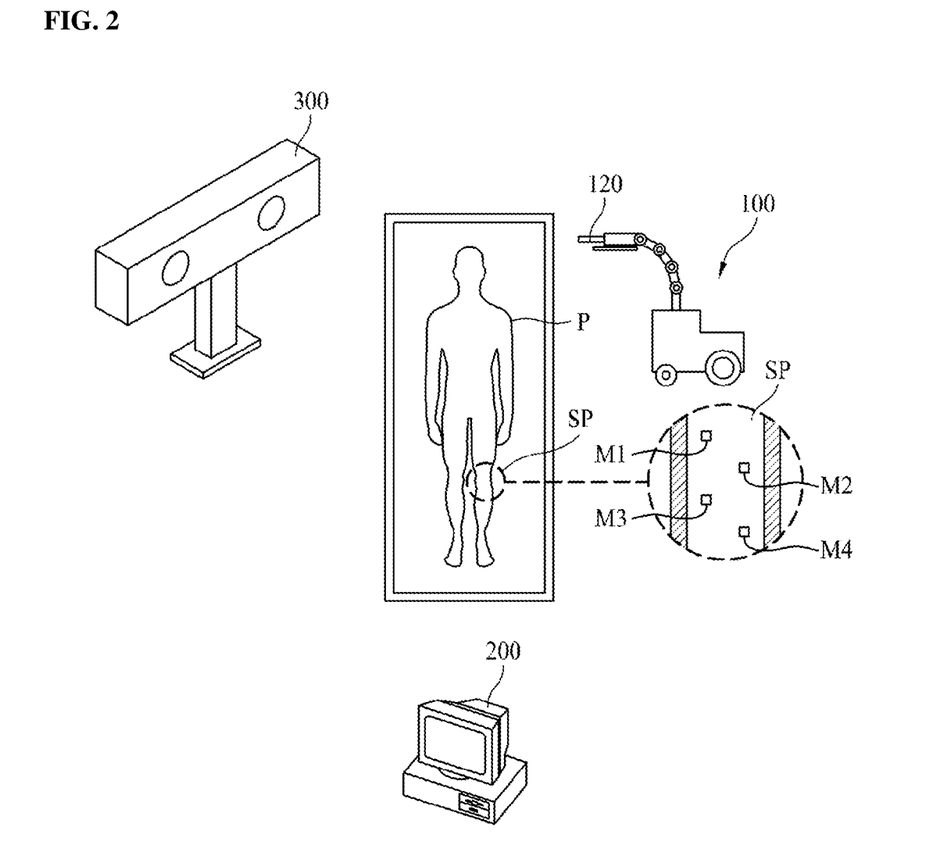
FIG. 2 is the rough view of the surgical robot system in accordance to the preferable embodiment of the present invention.

FIG. 1 and FIG. 2 are the control block diagram and the rough view of the surgical robot system in accordance to the preferable embodiment of the present invention, respectively.

With reference to the FIG. 1 and FIG. 2, the surgical robot system 10 in accordance to the preferable embodiment of the present invention comprises a surgical robot 100, a surgical path setting device 200, and a tracking device 300.

The surgical robot 100 which located in the operating room operates along predetermined first surgical path that has been transmitted from the surgical path setting device 200 and preset with respect to a surgical site SP of a person P to be operated on, and performs the operation for the surgical site.

The surgical robot 100 has operation control part (not illustrated) and robot arm 120. The operation control part sends the operation control command for the first surgical path to the robot arm 120, and then the 6-axis-driven robot arm 120 performs the surgery with the surgical instruments such as knife, cutter, drill, and the like attached to the end effector and with method.

The surgical path setting device 200 transmits the first surgical path to the surgical robot in advance. And if new surgical path should be reset during the operation of the surgical robot 100 or the monitoring of the surgical site, it transmits a surgical path reset command to the surgical robot 100 to make the surgical robot 100 stop the operation temporarily.

Also, the surgical path setting device 200 determines the new surgical path and transmits it to the surgical robot 100 so as to make the surgical robot 100 operate along the new surgical path and performs the operation for the surgical site continuously.

To perform the above, the surgical path setting device 200 might comprise communication part, monitoring part, and surgical path setting part. The procedure that the surgical path setting device 200 determines the new surgical path will be explained in detail referring to the FIGS. 3 and 4.

The tracking device 300 confirms the positions of the patient P and the surgical robot 100 before surgery and tracks the positions of the patient P and the surgical robot 100 during surgery. The tracking device 300 sends the positions of the patient P and the surgical robot 100 to the surgical path setting device 200 so that setting the surgical path before the surgery and monitoring the operation the surgery is possible.

In an embodiment, the tracking device 300 might be used with or without a marker.

For example, with the marker, the tracking device 300 might track the optical markers or the non-optical markers such as RF marker, magnetic marker and so on which are located in the patient P and the surgical robot 100. Without the marker, the tracking device 300 recognizes the objects such as the patient P and the surgical robot 100 and tracks the recognized objects.

Hereinafter, for the convenience of the explanation, assume that the tracking device 300 tracks the optical markers which are located in the patient P and the surgical robot 100.

The tracking device 300 might comprise an infrared light source and an infrared stereo camera that gets the tree-dimensional image of the object with separated two cameras. Also, optical markers M1, M2, M3 are located in the objects such as the patient P and the surgical robot 100, the positions of which should be confirmed. Each of optical markers has an infrared reflector to reflect the infrared light and is located in each of the surgical site of the patient P and the surgical robot 100. For example, in the case of operating the cut of femur and tibia around the knee before changing the knee joint, the optical marker M1 is located in the femur, M2 in the tibia, and M3 in the surgical robot 100 so that the tracking device 300 could track the positions of the femur, the tibia, and the surgical robot. The infrared reflectors of the optical markers M1, M2, M3 are patterned differently to make the tracking device 300 distinguish each of the makers and track the positions.

Except for the optical markers located in the surgical site and the surgical robot, an additional marker M4 to denote a specific position might be used to notify to the tracking device 300 the specific position. To determine the new surgical path in the present invention, the denoting optical marker M4 might be used to denote the surgical path reset position and input the denoted position to the tracking device 300. For example, after denoting multiple spots on the patient's body with the denoting optical makers M4 and inputting the denoted positions to the tracking device, the surgical path setting device 200 could set the new surgical path based on the input surgical path form and the input denoted positions.

Figure 3:
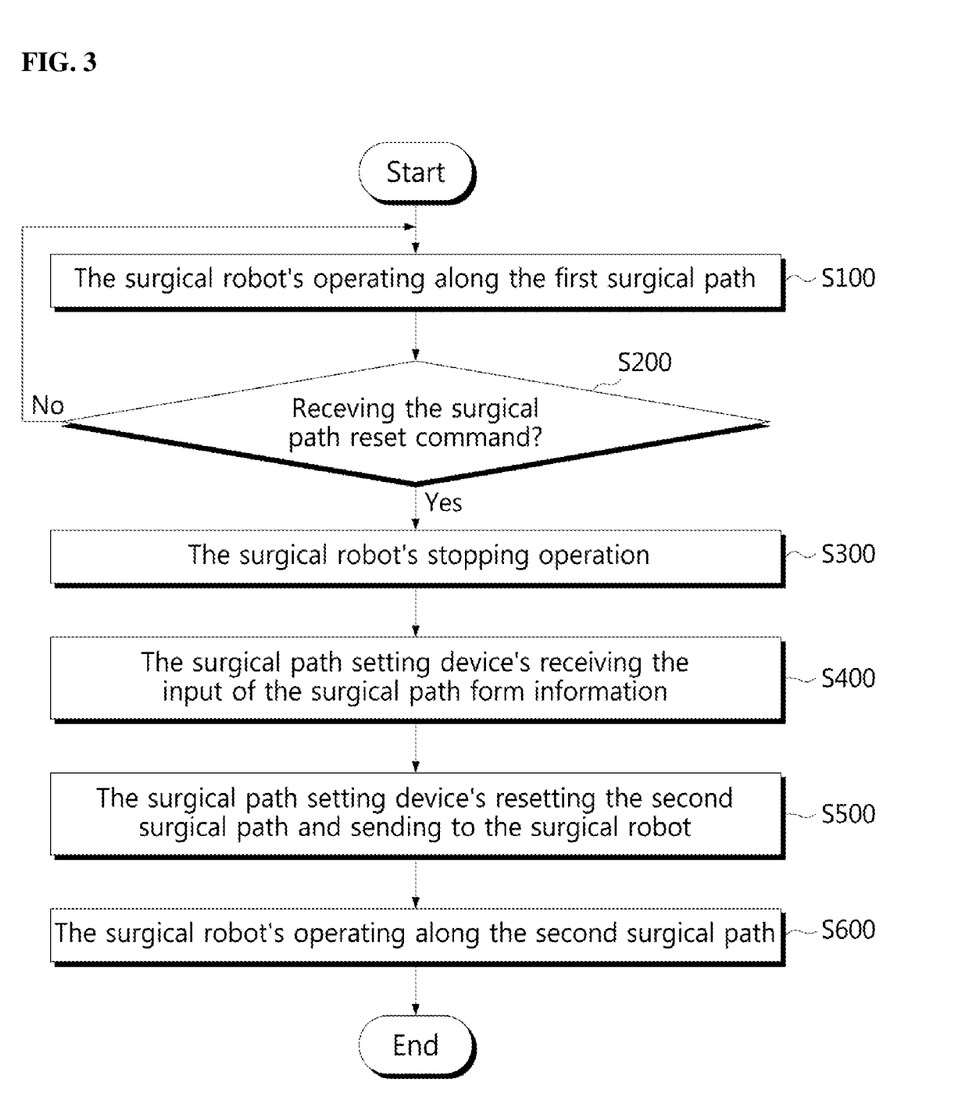
FIG. 3 is the flowchart of the surgical path setting method of the surgical robot in accordance to the preferable embodiment of the present invention.

FIG. 3 is the flowchart of the surgical path setting method of the surgical robot in accordance to the preferable embodiment of the present invention. With reference to the FIG. 3, in S100, the first surgical path is transmitted from the surgical path setting device 200 to the surgical robot 100 in advance, and the surgical robot 100 performs the operation for the surgical site along the first surgical path.

In S200, the surgical robot 100 confirms whether or not a surgical path reset command, transmitted from the surgical path setting device, has been received. If it is not received S100 is continued, but if it is received the operation of the surgical robot 100 is stopped in S300.

During the monitoring of the operation procedure and the working of the surgical robot 100, the surgical path reset command is input by the operator to make the surgical robot 100 stop the operation when the surgical site overlooked during the surgical planning is found during the surgery or the surgery should be operated with monitoring the surgical site directly.

In S400, the surgical path setting device 200 receives input of the surgical path form information. The surgical path form information is to provide the form of the surgical path suitable for the surgical site SP of the patient and to be implemented as a table below.

TABLE 1

| Basic form information | Detail form information | Form feature information |
| --- | --- | --- |
| Line | Straight line | Path designation or Specific direction designation |
|  | Curve | Arc or Free curve |
| Surface | Plane | Region designation or Surface designation |
|  | Curved surface | Spherical surface or Designated curved surface |

In S500, the surgical path setting device 200 determines a second surgical path, which is a new surgical path, on the basis of the surgical path form information according to the surgical path form and then transmits the second surgical path to the surgical robot 100. Here, the detail steps of the S500 will be explained below with reference with FIG. 4 and FIG. 5.

Figure 4:
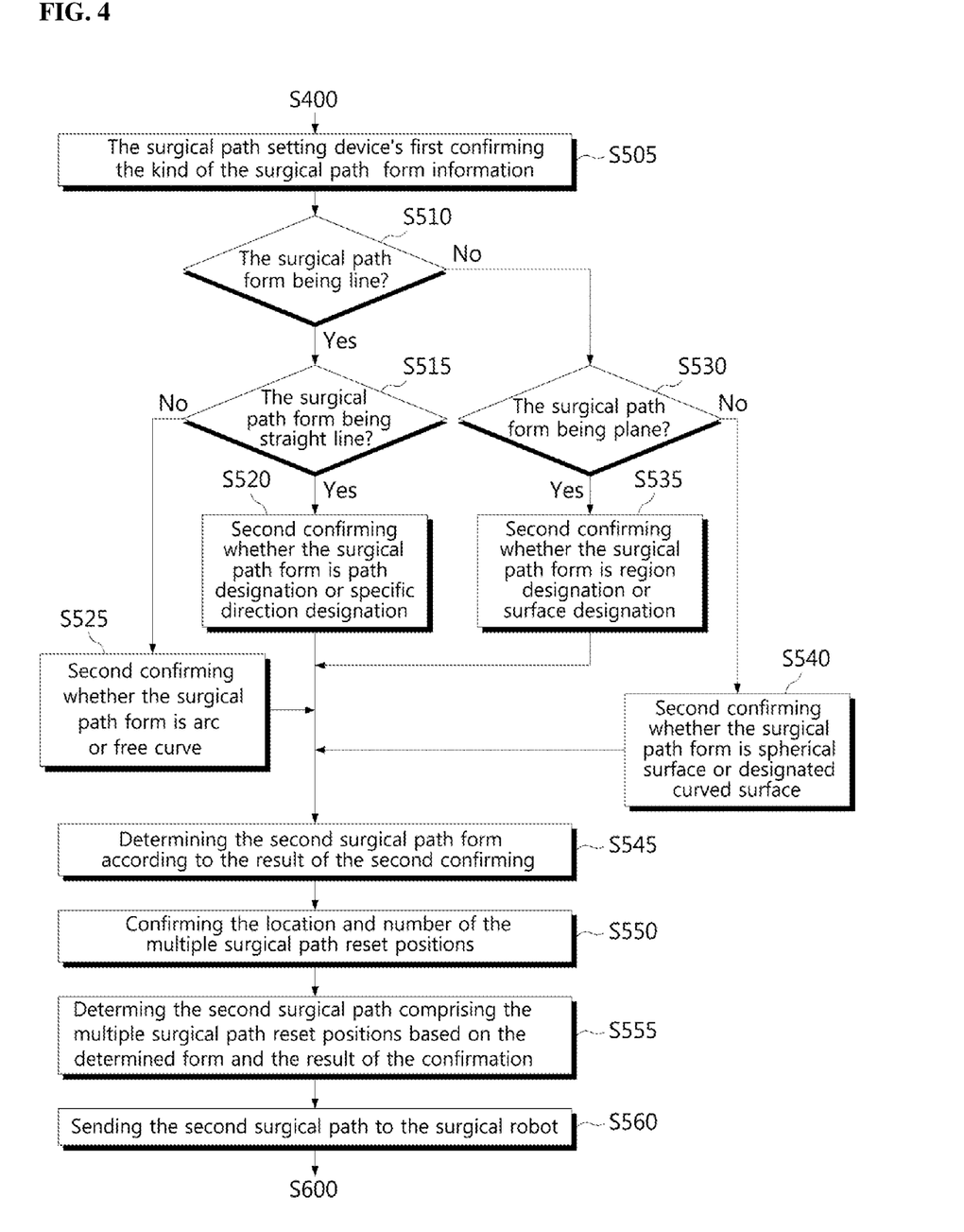
FIG. 4 is the specific flowchart of S500 of FIG. 3.
Figure 5:
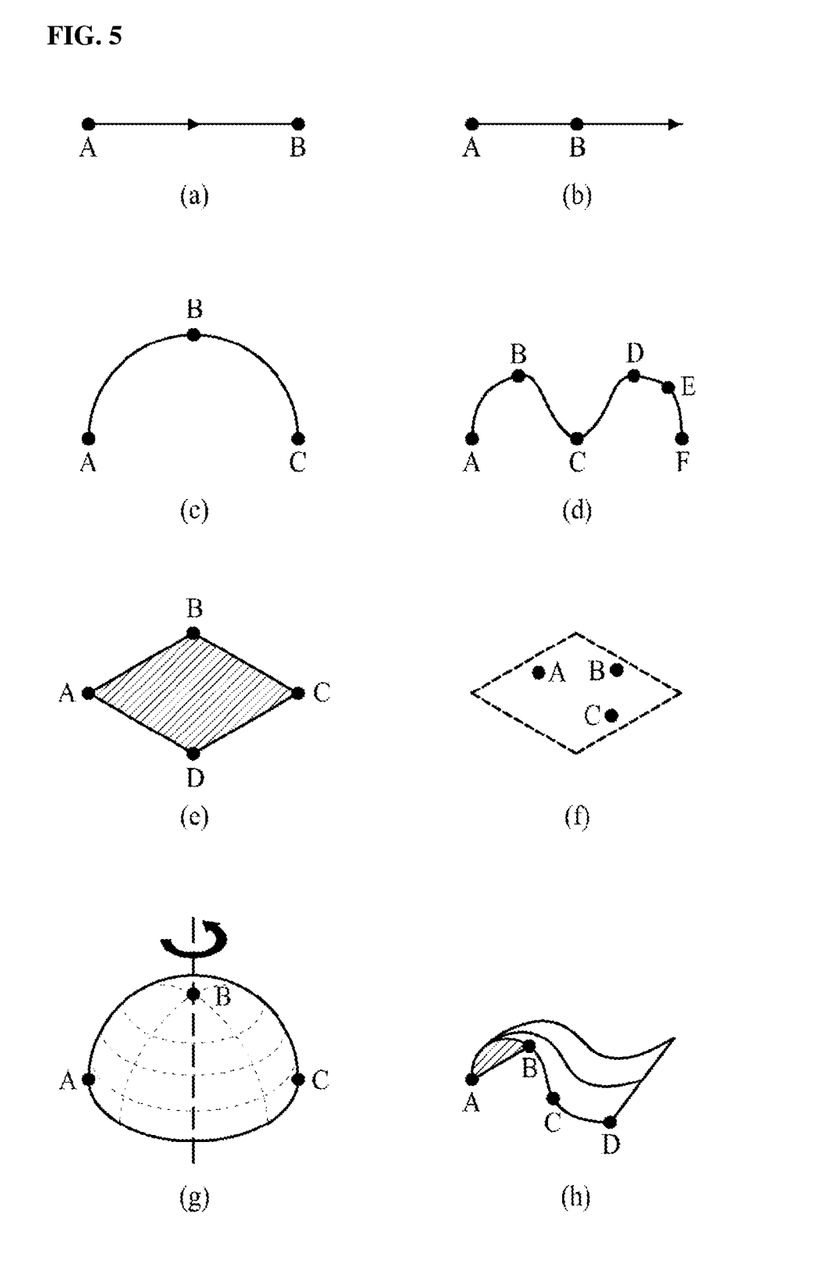
FIG. 5 is a reference drawing for the S555 of FIG. 4.

FIG. 4 is the specific flowchart of S500 of FIG. 3 and FIG. 5 is a reference drawing for the S555 of FIG. 4.

Referring to FIG. 4, in S505, the surgical path setting device 200 performs first confirmation of the kind of the surgical path form information, and then if the surgical path form is line in S510, confirms whether the surgical path form is straight line or not in S515.

If the surgical path form is straight line, the surgical path setting device 200 performs second confirmation of whether the surgical path form is path designation or specific direction designation in S520, and then the surgical path setting device 200 determines the form of the second surgical path according to the result of the second confirmation in S545.

However, if it is confirmed that the surgical path form is not straight line in S515, the surgical path setting device 200 determines that the surgical path form is curve and performs second confirmation of whether the surgical path form is arc or free curve in S525, and then the surgical path setting device 200 determines the form of the second surgical path according to the result of the second confirmation in S545.

Also, if it is confirmed that the surgical path form is not line in S510, the surgical path setting device 200 determines that the surgical path form is surface and confirms whether the surgical path form is plane or not in S530.

If the surgical path form is plane, the surgical path setting device 200 performs second confirmation of whether the surgical path form is region designation or surface designation in S535, and then the surgical path setting device 200 determines the form of the second surgical path according to the result of the second confirmation in S545.

However, if it is confirmed that the surgical path form is not plane in S530, the surgical path setting device 200 determines that the surgical path form is curved surface and performs second confirmation of whether the surgical path form is spherical surface or designated surface in S540, and then the surgical path setting device 200 determines the form of the second surgical path according to the result of the second confirmation in S545.

Accordingly, through S505-S545, the surgical path setting device 200 confirms the basic form information and detail form information of the surgical path form information and then determines the kind of the surgical path form first. (in other words, determining that the surgical path form is one of straight line, curve, plane, or curved surface) Then, it confirms the form feature information of the surgical path form information according to the result of the first determining and determines the surgical path form. (in other words, determining that the surgical path form is one of the path designation, the specific direction designation, the arc, the free curve, the region designation, the surface designation, the spherical surface or the designated curved surface)

In S550, the surgical path setting device 200 confirms the locations of the multiple surgical path reset positions.

Here, the locations of the multiple surgical path reset positions could be input as the denoted positions is input to the tracking device 300 using the denoting optical maker M4 to denote the multiple positions of the patient's body. For example, the denoting optical marker M4 is located in the specific position and then the operator inputs an input end command through input instrument (such as, pedal, keyboard, mouse, touch input panel and the like) to input the specific position. For the input of the multiple positions, the operator lays the denoting optical marker M4 in each of the multiple position and then inputs the input end command every time at each of the multiple position to input the multiple location to the tracking device 300.

In S555, the surgical path setting device 200 determines the second surgical path comprising the multiple surgical path reset positions according to the location and number of the multiple surgical path reset positions confirmed in S550 and the surgical path form determined in S545.

In other words, referring to the FIG. 5, in S555 the surgical path setting device 200 confirms the location and number of the multiple surgical path reset positions and then determines the second surgical path such like the form in FIG. 5(a) if the surgical path form is line and path designation, the form in FIG. 5(b) if the surgical path form is line and specific direction designation, the form in FIG. 5(c) if the surgical path form is curve and arc, or the form in FIG. 5(d) if the surgical path form is free curve.

Also, the surgical path setting device 200 confirms the location and number of the multiple surgical path reset positions and then determines the second surgical path such like the form in FIG. 5(e) if the surgical path form is plane and region designation, the form in FIG. 5(f) if the surgical path form is plane and surface designation, the form in FIG. 5(g) if the surgical path form is curved surface and spherical surface, or the form in FIG. 5(h) if the surgical path form is curved surface and designated curved surface.

In S560, the surgical path setting device 200 sends the second surgical path reset in S555 to the surgical robot 100 and then the S500 is finished and S600 is performed.

In other embodiment, if the surgical path setting device 200 sets the second surgical path, virtual object for the second surgical path could be generated and assist the manual surgery of the operator.

For example, when the surgical robot 100 does not perform the automatic surgery operation but the operator handles and drives the surgical robot 100 manually to operate directly, the virtual object for the reset second surgical path is set in the surgical path setting device 200 to limit the working of the surgical robot 100.

In one embodiment, if the reset second surgical path is set as a desirable surgical path, virtual object to prevent the surgical robot 100 from deviating from the second surgical path is set to the surgical path setting device 200 so that the surgical robot 100 which is handled by the operator is prevented from the deviating from the second surgical path.

If the reset second surgical path is set as a prohibited surgical path, virtual object to prevent the surgical robot 100 from invading into the second surgical path is set to the surgical path setting device 200 so that the surgical robot 100 which is handled by the operator is prevented from the invading into the second surgical path.

Although the invention has been shown and described with reference to certain exemplary embodiments thereof, the present invention is not limited by the embodiments described above. The various modifications can be made based on the described embodiments and the illustrated figures by those skilled in the art without departing from the spirit and scope of the invention as defined by the appended claims.

What is claimed is:

1. A surgical robot system, comprising:
   a surgical robot operating along a first surgical path with respect to a surgical site of a patient;
   a surgical path setting device transmitting information of the first surgical path to the surgical robot and transmitting a surgical path reset command to the surgical robot, when the first surgical path needs to be reset, to make the surgical robot stop operation temporarily; and
   a tracking device confirming positions of the surgical site of the patient and the surgical robot before a surgery and tracking the positions of the surgical site of the patient and the surgical robot during the surgery,
   wherein the surgical path setting device resets the first surgical path to a second surgical path based on a location and the number of multiple surgical path reset positions and surgical path form information during the surgery; and
   wherein the surgical path form information includes at least one of a straight line, a curved line, a plane, or a curved surface.

2. A surgical path setting device, comprising one or more processors configured to:
   transmit to a surgical robot information of a first surgical path with respect to a surgical site of a patient to command operation of the surgical robot,
   receive positions of the surgical site of the patient and the surgical robot from a tracking device before a surgery, and
   reset the first surgical path to a second surgical path based on a location and the number of multiple surgical path reset positions and surgical path form information during the surgery, and
   wherein the surgical path form information includes at least one of a straight line, a curved line, a plane, and a curved surface.

3. The device according to claim 2, wherein the one or more processors are further configured to:
   first confirm a first class of the surgical path form information;
   second confirm a second class of the surgical path form information according to the first class of the surgical path form information, and
   determine a form of a second surgical path according to the second class of the surgical path form information.

4. The device according to claim 3, wherein the one or more processors are further configured to:
   select one of the straight line, the curve, the plane, and the curved surface for the first class of the surgical path form information according to the result of the first confirming.

5. The device according to claim 3, wherein the one or more processors are further configured to:
   second confirm whether the second class of the surgical path form information is a path designation or a specific direction designation if the first confirmed class of the surgical path form information is the straight line; and
   determine the second surgical path form based on the result of the second confirming.

6. The device according to claim 3, wherein the one or more processors are further configured to:
   second confirm whether the second class of the surgical path form information is an arc or a free curve if the first confirmed class of the surgical path form information is the curved line; and
   determine the second surgical path form based on the result of the second confirming.

7. The device according to claim 3, wherein the one or more processors are further configured to:
   second confirm whether the second class of the surgical path form information is a region designation or a surface designation if the first confirmed class of the surgical path form information is the plane; and
   determine the second surgical path form based on the result of the second confirming.

8. The device according to claim 3, wherein the one or more processors are further configured to:
   second confirm whether the second class of the surgical path form information is a spherical surface or a designated curved surface if the first confirmed class of the surgical path form information is the curved surface; and
   determine the second surgical path form based on the result of the second confirming.

9. A surgical path setting method comprising the steps of:
   (a) operating a surgical robot along a first surgical path, wherein information of the first surgical path has been transmitted from a surgical path setting device;
   (b) confirming whether or not a surgical path reset command, transmitted from the surgical path setting device, has been received;
   (c) stopping operation of the surgical robot when the surgical path reset command has been received;
   (d) receiving, by the surgical path setting device, an input of surgical path form information;
   (e) determining, by the surgical path setting device, a second surgical path on a basis of a location and the number of multiple surgical path reset positions and the surgical path form information and then transmitting information of the second surgical path to the surgical robot; and
   (f) operating the surgical robot along the second surgical path,
   wherein the surgical path form information includes at least one of a straight line, a curved line, a plane, and a curved surface.

10. The method according to claim 9, wherein the step (e) comprises:
- (e1) first confirming a first class of the surgical path form information;
- (e2) second confirming a second class of the surgical path form information according to a result of the first confirming, and determining a form of the second surgical path according to a result of the second confirming;
- (e3) confirming the location and the number of multiple surgical path reset positions;
- (e4) determining the second surgical path including the multiple surgical path reset positions according to the determined form thereof; and
- (e5) transmitting information of the determined second surgical path to the surgical robot.

11. The method according to claim 10, wherein the step (e1) comprises:
selecting one of the straight line, the curved line, the plane, and the curved surface for the first class of the surgical path form information according to the result of the first confirming.

12. The method according to claim 11, wherein the step (e2) comprises:
second confirming whether the second class of the surgical path form information is a path designation or a specific direction designation if the first confirmed class of the surgical path form information is the straight line and determining the second surgical path form based on the result of the second confirming.

13. The method according to claim 11, wherein the step (e2) comprises:
second confirming whether the second class of the surgical path form information is an arc or a free curve if the first confirmed class of the surgical path form information is the curved line, and determining the second surgical path form based on the result of the second confirming.

14. The method according to claim 11, wherein the step (e2) comprises:
second confirming whether the second class of the surgical path form information is a region designation or a surface designation if the first confirmed class of the surgical path form information is the plane, and determining the second surgical path form based on the result of the second confirming.

15. The method according to claim 11, wherein the step (e2) comprises:
second confirming whether the second class of the surgical path form information is a spherical surface or a designated curved surface if the first confirmed class of the surgical path form information is the curved surface, and determining the second surgical path form based on the result of the second confirming.

* * * * *